(12) United States Patent
Cantrell

(10) Patent No.: US 9,757,068 B2
(45) Date of Patent: Sep. 12, 2017

(54) WIRELESS PLAY COMMUNICATION WRISTBAND

(71) Applicant: Travis Lee Cantrell, Savage, MN (US)

(72) Inventor: Travis Lee Cantrell, Savage, MN (US)

( * ) Notice: Subject to any disclaimer, the term of this patent is extended or adjusted under 35 U.S.C. 154(b) by 0 days.

(21) Appl. No.: 14/811,441

(22) Filed: Oct. 20, 2015

(65) Prior Publication Data

US 2016/0158639 A1 Jun. 9, 2016

(51) Int. Cl.
| | |
|---|---|
| *A63F 9/24* | (2006.01) |
| *F21V 33/00* | (2006.01) |
| *F21V 15/04* | (2006.01) |
| *G08B 5/36* | (2006.01) |
| *A61B 5/00* | (2006.01) |
| *G09F 3/00* | (2006.01) |
| *H04B 1/3827* | (2015.01) |
| *G09F 21/02* | (2006.01) |
| *G09F 23/00* | (2006.01) |
| *G09F 13/22* | (2006.01) |

(52) U.S. Cl.
CPC .............. *A61B 5/681* (2013.01); *G09F 3/005* (2013.01); *G09F 21/02* (2013.01); *G09F 23/0066* (2013.01); *H04B 1/385* (2013.01); *G09F 2013/222* (2013.01); *H04B 2001/3861* (2013.01)

(58) Field of Classification Search
None
See application file for complete search history.

(56) References Cited

U.S. PATENT DOCUMENTS

| | | | | |
|---|---|---|---|---|
| 5,959,281 A | * | 9/1999 | Domiteaux | G09B 5/062 235/375 |
| 7,168,098 B2 | * | 1/2007 | West | A41D 27/20 2/247 |
| 8,062,037 B1 | * | 11/2011 | Chapa, Jr. | A63B 43/008 434/251 |
| 8,156,571 B2 | * | 4/2012 | Barzilla | A63B 71/143 2/19 |
| 8,608,478 B2 | * | 12/2013 | Luster | A63B 24/0021 434/247 |
| D701,001 S | * | 3/2014 | Daniel | D29/120.1 |
| 8,793,321 B2 | * | 7/2014 | Williams | A63B 71/06 463/42 |
| 8,845,461 B2 | * | 9/2014 | Duke | A63B 69/0071 473/447 |

(Continued)

*Primary Examiner* — Quan-Zhen Wang
*Assistant Examiner* — Chico A Foxx
(74) *Attorney, Agent, or Firm* — Garrett James O'Sullivan

(57) ABSTRACT

This invention is intended to strengthen play transmission between players and coaches before, and during plays.
The wristband is an elastic, or adjustable wristband with a clear plastic window and LED strips or LED matrix that lights the Light Emitting Diode (LED) next to a desired play. The wristband is wirelessly linked to either a radio frequency panel, bluetooth device, or infrared controller. The wristband LED's are wired to a microcontroller, Bluetooth controller (or RF transceiver, or Infrared controller), and a battery power source. The LED's are displayed through the clear plastic window and the plays are slid over the top of the LED's. The micro controller, battery and wireless controller are contained in a velcro-enclosed, low-profile enclosure opposite the clear plastic window.

2 Claims, 2 Drawing Sheets

(56) References Cited

U.S. PATENT DOCUMENTS

Figure 1:
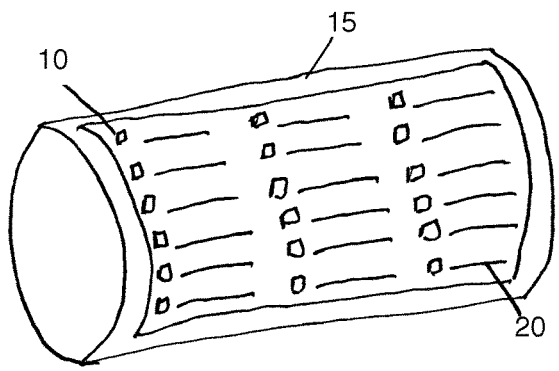

| | | | |
|---|---|---|---|
| 8,904,951 B1* | 12/2014 | Hronek | A63B 71/0669 116/223 |
| 9,129,541 B2* | 9/2015 | Weiler | G09G 5/00 |
| 9,584,641 B2* | 2/2017 | Mestre | H04M 1/22 |
| 2007/0143382 A1* | 6/2007 | Luster | A63B 24/0021 708/100 |
| 2007/0290801 A1* | 12/2007 | Powell | G08B 1/08 340/7.55 |
| 2008/0206723 A1* | 8/2008 | Hunter | G09B 19/0007 434/156 |
| 2008/0317263 A1* | 12/2008 | Villarreal, Jr. | A42B 3/30 381/120 |
| 2010/0080388 A1* | 4/2010 | Daniel | A63B 71/06 380/270 |
| 2010/0080389 A1* | 4/2010 | Daniel | A63B 71/06 380/270 |
| 2011/0218043 A1* | 9/2011 | Quillen, III | A63F 13/812 463/37 |
| 2016/0206083 A1* | 7/2016 | Gomez | A45F 5/00 224/219 |

\* cited by examiner

WIRELESS PLAY COMMUNICATION WRISTBAND

FIELD OF THE INVENTION

This invention is a device that strengthens the play transmission and understanding between players and coaches during game play.

BACKGROUND OF THE INVENTION

Coaches are always trying to communicate plays or certain aspects of plays during a game to their players. Some coaches use a play sheet and a numbered play sheet wristband to signal plays,
some coaches use hand signals to transmit plays to players, some coaches use storyboards with figures and hand signals to send plays to players. These methods of sending play information are archaic at best. Often times signals are confused resulting in the wrong play being called.

This invention solves the play communication problems. The coach is able to press a button on a wireless Bluetooth/Radio Frequency/Infrared device and light the corresponding LED on the player's wristband.

SUMMARY OF THE INVENTION

The invention relates to strengthening coach to player communication during a sporting event presenting light emitting diodes (LED) lights associated with corresponding plays inserted next to or over the LED lights signifying a correct play call.

The invention is a wristband of elastic, or adjustable design with a clear, see-through plastic window displaying the LED lights and corresponding plays, and a velcro enclosure opposite the clear plastic window, which houses the electric components: microcontroller, RF/IR/XBEE/Bluetooth wireless controller, battery power supply.

The wristband invention will link wirelessly with any wireless device that a coach uses to transmit a signal to light the play LED on the invention (player's wristband). The wristband will link with Bluetooth on a cellular device, Radio Frequency or XBEE from an RF panel, or an Infrared device, by changing out the corresponding wireless Bluetooth, XBEE or RF transceiver, Infrared receiver in the wristband enclosure wired to the microcontroller and the battery power source.

A coach presses a button on his wireless device and the signal is received via the wristband's wireless receiver and the signal is interpreted by the microcontroller (powered by the battery power source), and sends the signal to an appropriate LED to light next to a desired play.

This invention is useful to almost any sport where a coach needs to send plays in to players on the field/court/pitch.

BRIEF DESCRIPTION OF THE DRAWING FIGURES

Figure 2:
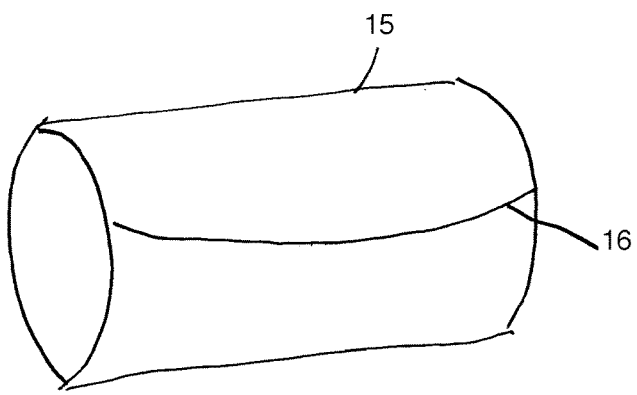
Figure 3:
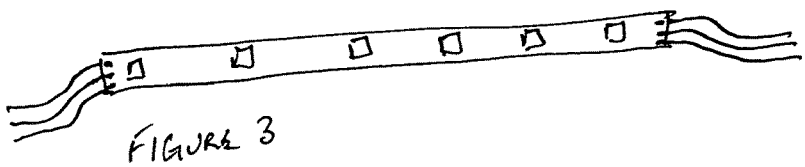
Figure 4:
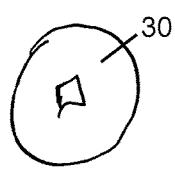
Figure 5:
Figure 6:
Figure 7:
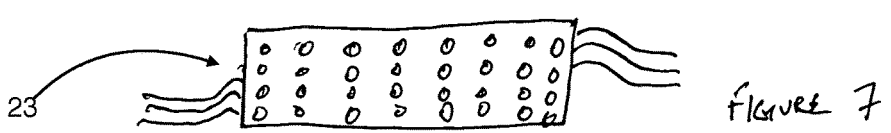
Figure 8:
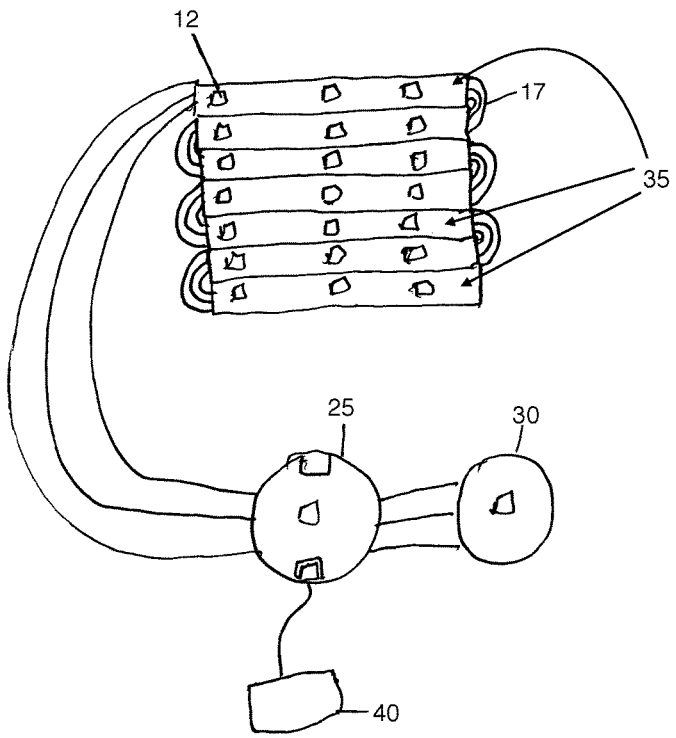
Figure 9:
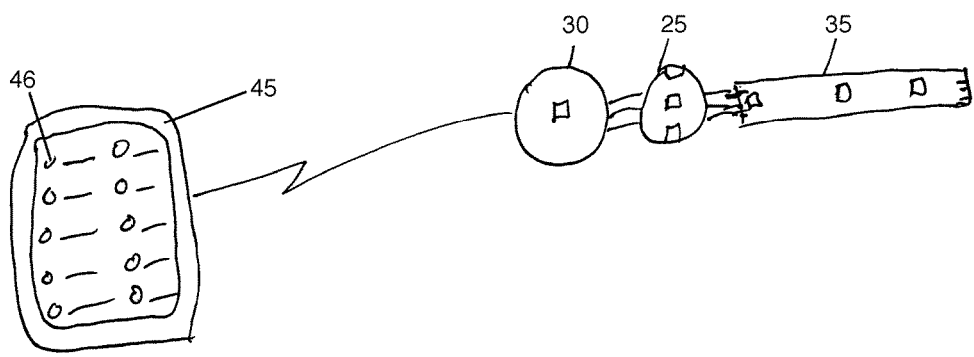

FIG. 1 is an illustrative view of the top side of wristband invention.
FIG. 2 is an illustrative view of the bottom side of wristband invention.
FIG. 3 is an illustrative view of the Programmable LED Strip.
FIG. 4 is an illustrative view of the wireless controller.
FIG. 5 is an illustrative view of the microcontroller.
FIG. 6 is an illustrative view of the Battery power supply.
FIG. 7 is an illustrative view of the LED Matrix.
FIG. 8 is an illustrative of a circuit assembly of the wireless wristband apparatus according to an embodiment of the present invention.
FIG. 9 is an illustrative view of the communication process according to an embodiment of the present invention.

DETAILED DESCRIPTION OF THE PREFERRED EMBODIMENT

The following discussion describes in detail an embodiment of the wireless play wristband apparatus. This discussion should not be construed, however, as limiting the invention to this particular embodiment.

FIG. 1 is an illustrative view of the top side of the wristband invention illustrating a first LED 10 of a LED matrix. FIG. 1 also illustrates the wristband 15, which is made of elastic, or adjustable material. The LED Matrix is covered by a clear (see through) plastic window. There is also a slot to slide plays between the LED Matrix and the clear plastic window. A player will be able to see the LED light next to the corresponding play 20 through the clear plastic window on the top of the wristband 15.

FIG. 2 is an illustrative view of the bottom of the wristband invention. FIG. 2 illustrates a velcro enclosure that will house the electronic components for wireless communication and LED controls.

FIG. 3 is an illustrative view of a programmable LED strip. Several LED strips can be wired together to create a Matrix, or an LED Matrix can be used (FIG. 7; LED Matrix 23).

FIG. 4 is an illustrative view of a Bluetooth universal asynchronous receiver/transmitter (UART) wireless controller 30. The Bluetooth UART wireless controller 30 will accept Bluetooth pairing for remote wireless connectivity from a cell phone, or tablet (or any Bluetooth paired device). The Bluetooth UART wireless controller 30 is wired to a microcontroller.

A Radio Frequency (RF), or XBEE, or Infrared (IR) device may also be used for wireless connectivity.

While certain novel features of this invention have been described in the Detailed Descriptions above, it is not intended to be limited to said details, since it will be understood that various omissions, changes, and substitutions in the forms of details of the device illustrated and in its operation can be made by those skilled in the art without departing in any way from the spirit of the wristband invention.

FIG. 5 is an illustrative view of a microcontroller 25. This microcontroller 25 contains the programming allowing the wireless controller (Bluetooth, RF, IR, XBEE) to connect and control the LED Matrix within the wristband.

FIG. 6 is an illustrative view of a power source 40. The power source 40 is typically a 3.3V or 5V power source. The power source 40 is rechargeable via Universal Serial Bus (USB) connection to a PC or another USB power source.

FIG. 7 illustrates the LED Matrix 23.

FIG. 8 is an illustrative view of a circuit assembly. FIG. 8 illustrates a first LED 12 on a LED strip 35. FIG. 8 also illustrates the wiring 17 between each LED strip 35 (an LED Matrix may also be used, see FIG. 7). Three wires connect each LED strip and eventually connect to the microcontroller 25, then the microcontroller 25 is wired to the wireless controller 30.

FIG. 9 is an illustrative view of the communication process. FIG. 9 illustrates a button 46 on a remote wireless device 45 (cell phone, RF, XBEE, IR transmitter). The remote wireless device 45 pairs with the wireless controller 30 on the wristband, then the wireless controller 30 passes a received signal through to the microcontroller 25, which sends a signal to the programmable LED strip 35. Therefore, the first LED 12 of FIG. 8 is lit when the button 46 is pressed on the wireless wristband.

What is claimed is:

1. A play call communication system comprising:
   a wristband having a defining and adjustable opening, the wristband comprising:
   an enclosure having a transparent window and at least one slot configured to accept plays, wherein the plays are slid into the enclosure via the at least one slot to be displayed via a insertion, and each play of the plays is displayed at a particular location respectively;
   a microcontroller;
   at least one wireless controller in communication with the microcontroller to provide transmitted one or more signals to the microcontroller;
   a power supply to provide power to the microcontroller and the wireless controller; and
   a plurality of light emitting diodes (LEDs) each corresponding to a particular play of the plays displayed with respect to the particular location of that play, wherein the plays are disposed between the plurality of LEDs and the transparent window once the plays have been inserted to permit the plays to be displayed via the transparent window, wherein a determined play of the plays is selectively indicated by at least one lit LED under control of the microcontroller responsive to a received command corresponding to the determined play, and wherein the microcontroller, the at least one wireless controller, the power supply, and the plurality of LEDs are entirely within the enclosure; and
   a remote wireless communication device in communication with the wristband based on a selection corresponding to the determined play amongst the plays, wherein the remote wireless communication device transmits said one or more signals, and wherein the one or more signals comprise said command corresponding to said determined play to the wireless controller to select said at least one lit LED to indicate the determined play amongst the plays on the wristband via the transparent window.

2. The system of claim 1, wherein the determined play is indicated through a method comprising the steps of:
   a player performing the insertion of the plays into the at least one slot;
   a coach determining the determined play to be indicated, by the coach selecting and pressing the at least one button on the remote wireless communication device indicative of the selection corresponding to the determined play amongst the plays;
   the remote wireless communication device transmitting the one more signals based on the selected at least one button to the wireless controller;
   the wireless controller receiving the one or more signals, wherein the one or more signals are interpreted by the microcontroller;
   the microcontroller lighting the at least one lit LED, wherein the at least one lit LED is substantially close to the determined play, wherein the at least one lit LED indicates the determined play to the player.

* * * * *